United States Patent [19]

Klein et al.

[11] 4,110,077

[45] Aug. 29, 1978

[54] DETERMINATION OF β-LIPOPROTEINS IN BLOOD SERUM WITH POLYANETHOLE SULFONATE

[75] Inventors: Bernard Klein, New Hyde Park, N.Y.; James Arthur Foreman, Montclair, N.J.

[73] Assignee: Hoffmann-La Roche Inc., Nutley, N.J.

[21] Appl. No.: 731,057

[22] Filed: Oct. 8, 1976

[51] Int. Cl.² ............... G01N 33/16; G01N 31/02; G01N 21/22
[52] U.S. Cl. ................. 23/230 B; 260/112 B
[58] Field of Search .............. 23/230 B; 252/408; 260/112 B

[56] References Cited

U.S. PATENT DOCUMENTS

| | | | |
|---|---|---|---|
| 3,894,844 | 7/1975 | Pinto | 23/230 B |
| 3,954,409 | 5/1976 | Hsia | 23/230 B |
| 3,955,925 | 5/1976 | Proksch | 260/112 B X |
| 3,958,939 | 5/1976 | Jones | 23/230 B |
| 3,958,939 | 5/1976 | Jones | 260/112 B X |
| 3,960,493 | 6/1976 | Beitz | 23/230 B |
| 3,993,585 | 11/1976 | Pinto | 23/230 B |
| 4,001,089 | 1/1977 | Stavropoulos | 23/230 B X |
| 4,011,045 | 3/1977 | Bonderman | 23/230 B |
| 4,012,196 | 3/1977 | Frings | 23/230 B |
| 4,012,287 | 3/1977 | Carl | 23/230 B |
| 4,045,176 | 8/1977 | Proksch | 260/112 B X |

OTHER PUBLICATIONS

Chemical Abstracts, 73:118082p (1970).
Chemical Abstracts, 75:149579b (1971).
M. Burstein et al., Adv. Lipid Res., 11, 67–108 (1973).

*Primary Examiner*—Sidney Marantz
*Attorney, Agent, or Firm*—Samuel L. Welt; Bernard S. Leon; R. Hain Swope

[57] ABSTRACT

A process of isolating beta-lipoproteins from blood serum in about 99% purity comprising precipitating beta-lipoproteins from blood serum substantially free of chylomicrons with polyanethole sulfonate and a divalent cation, forming a solution of the beta-lipoproteins and reprecipitating them with the divalent cation, again forming a solution of said beta-lipoproteins and passing them through a DEAE cellulose column. The beta-lipoproteins purified by the method are particularly suited as a calibration standard for use in assays of the beta-lipoprotein content of blood serum.

3 Claims, No Drawings

"DETERMINATION OF β-LIPOPROTEINS IN BLOOD SERUM WITH POLYANETHOLE SULFONATE"

BACKGROUND OF THE INVENTION

It is generally agreed that hyperlipidemia is a predisposing factor to cardiovascular disease. Lipids are present in the blood serum as lipoproteins. The lipoproteins specifically implicated in cardiovascular disease are classified as low density lipoproteins (LDL) and very low density lipoproteins (VLDL) according to their ultracentrifugal flotation properties, and as beta- and pre-beta lipoproteins, respectively, according to their electrophoretic migration. In addition to the fact that there are various means of classifying lipoproteins, there are a number of recognized methods for isolating and purifying them.

Most lipoprotein purification methods utilize ultracentrifugation either alone or subsequent to a preliminary precipitation of the serum lipoprotein fraction with, e.g. polyanion and a divalent cation. This is a difficult and involved technical operation. The lipoproteins are then classified by one of the methods referred to above. The entire procedure of purifying and classifying lipoproteins is not only difficult but also time consuming.

The quantitative determination of serum beta-lipoproteins is a very valuable medical diagnostic tool. A rapid screening procedure for detecting increased serum beta-lipoprotein levels would be an even more valuable medical diagnostic tool since it would facilitate a means of identifying individuals with occult hyperlipidemia, thereby indicating the need for further and more definitive examination of their blood serum for cholesterol and triglyceride levels. One procedure commonly utilized for determination of serum low density lipoproteins is a turbidimetric estimation. In this method, the turbidity (absorbance) of a sample of serum from an individual who has fasted 18 hours is determined after it has been treated to precipitate the low density beta-lipoproteins by the addition of both a divalent cation, i.e. $Ca^{++}$ and a polyanion precipitant. A similar amount of serum is treated with the same volume of reagent containing only the divalent cation. The turbidity (absorbance) of this second solution (reagent blank) is subtracted from the first reading. The turbidity values are expressed in arbitrary absorbance units.

A number of precipitants are described in the art for use in turbidimetric determinations. The preferred reagents for this purpose are polyanions which are utilized in conjunction with a divalent cation. Frequently used polyanions include, for example, dextran sulfate, heparin, amylopectin sulfate and phosphotungstate. Divalent cations commonly utilized include $Ca^{++}$, $Mg^{++}$, and $Mn^{++}$. The procedures utilizing such materials in the turbidimetric determinations are fully described by Burstein and Scholnick: Lipoprotein-polyanion-metal interactions. *Adv. Lipid Res.* 11. 67 (1973). In this article, Burstein et al mention the use of numerous sulfated polyanions as precipitants for the removal of the beta-lipoprotein fraction from serum. The authors include under this heading sodium polyanethole sulfonate which is incorrect because sodium polyanethole is a polysulfonate as opposed to a polysulfated molecule. In addition, Burstein et al. give no suggestion that sodium polyanethole sulfate could be utilized to prepare a calibration standard which would facilitate the quantitative determination of serum beta-lipoproteins.

The present invention describes the preparation of low- and very low-density serum beta-lipoproteins of immunochemical homogeneity. Beta-lipoproteins prepared in accordance with the invention are useful as calibration standards in the turbidimetric determination of serum beta-lipoproteins. Such determinations performed as described using the calibration standard provided in accordance with the invention have been shown to yield quantitative results and to be, unexpectedly, relatively free from interference from chylomicrons present in the serum.

BRIEF DESCRIPTION OF THE INVENTION

In accordance with the present invention, a calibration standard for the determination of blood serum beta-lipoproteins is provided by treating the serum with polyanethole sulfonate in the presence of a divalent cation, e.g. magnesium ion, to precipitate the beta-lipoproteins and subsequent passage thereof through a DEAE-cellulose column.

DETAILED DESCRIPTION OF THE INVENTION

In accordance with the present invention, blood serum is treated to isolate the beta-lipoproteins therein and purify them to immunochemical homogeneity. The purified beta-lipoproteins thus prepared constitute an improved calibration standard useful in the determination of serum beta-lipoprotein concentration by methods recognized in the art, e.g. turbidimetric determination. Further, the invention pertains to a reagent kit containing the calibration standard described.

The initial step in the treatment of blood serum in accordance with the present invention is precipitation of serum beta-lipoproteins with polyanethole sulfonate. A sample of normal serum is treated with about an equal volume of an aqueous solution of polyanethole sulfonate. Generally, a solution of from about 0.35% by weight to about 0.75% by weight, preferably about 0.5% by weight polyanethole sulfonate is utilized. To the resulting mixture is added a sufficient amount of a water-soluble salt of a divalent cation to provide from about 0.05 moles to about 0.15 moles per liter, preferably about 0.1 moles per liter of said divalent cation. While other divalent cations such as, for example, $Ca^{++}$ and $Mn^{++}$ can be utilized in the practice of the invention, the preferred divalent cation is $Mg^{++}$. Of the water-soluble salts of such divalent cations recognized in the art, the chloride is preferred. After the solution containing the sodium polyanethole sulfonate and divalent cation has been added to the sample of serum with stirring, the mixture is allowed to stand for from 1 to 3 hours. The precipitated protein is resuspended in an aqueous solution of tetrasodium ethylenediaminetetraacetate. After warming the mixture, an additional quantity of the same divalent cation is added to reprecipitate the protein. The protein is again suspended in $Na_4EDTA$ solution and dialyzed. An appropriate quantity of protein is then passed through a column packed with DEAE-cellulose. The resulting highly purified beta-lipoprotein is then assayed for protein and cholesterol content and the concentration adjusted to a predetermined level for use as a calibration standard.

In the preparation of the calibration standard of this invention the sodium polyanethole sulfonate separates beta-lipoproteins from the other serum proteins as a roughly 90% beta-lipoprotein mixture since some other proteins, i.e. albumin are removed by physical entrapment. Reprecipitation produces a mixture about 95% beta-lipoprotein and passage through the DEAE cellulose column results in a purity of 99% and above. The calibration standard contains no chylomicrons since they are not precipitated from the serum in the first precipitation of beta-lipoprotein. It has been established by careful analysis that the calibration standard is a very pure mixture of material within a very narrow range and is composed of very low density lipoproteins (VLDL) and low density lipoproteins (LDL). The preparation of a standard of such purity is possible since the method of the subject invention does not coprecipitate chylomicrons, high density lipoproteins and other globulins from the serum.

The highly purified beta-lipoprotein material produced by the above described procedure has been shown to be a superior calibration standard for the turbidimetric determination of plasma beta-lipoprotein concentration, particularly in view of the fact that use of applicant's calibration standard in turbidimetric lipoprotein assays appears to be essentially unaffected by the presence of unusually high percentages of chylomicrons in the serum being tested.

The calibration standard of the present invention is intended to be one reagent in a reagent kit which also contains a reagent blank solution, viz. an aqueous solution of the divalent cation, e.g. magnesium chloride, and a third reagent which is an aqueous solution of polyanethole sulfonate and the divalent cation additionally containing a suitable amount of a preservative, e.g. 0.02% by weight sodium azide, and the like. This latter solution and the reagent blank solution can, if desired for convenience in shipping, be packaged either as a powder or in a concentrated liquid form which is dilutable to the concentration to be utilized in the test. Utilizing the reagent kit calibration curve can be readily established by adding appropriate aliquots of the calibration standard preparation to the sodium polyanethole sulfonate reagent and measuring the turbidity. Because of the purity of the calibration standard of the present invention, the calibration curve will be linear with reference to increasing lipoprotein content. A sample of serum to be analyzed is mixed with the sodium polyanethole sulfonate reagent, allowed to incubate and the turbidity determined. The beta-lipoprotein content of the serum is accurately determined by comparing the measured turbidity against the calibration curve. If the sera to be tested is cloudy or turbid, a serum blank may be prepared by mixing the serum with the reagent blank solution, i.e. the solution containing the divalent cation and measuring the turbidity thereof to obtain a correction factor.

Because the beta-lipoprotein calibration standard prepared in accordance with the present invention is of immunochemical homogeneity and facilitates the preparation of a linear calibration of protein concentration, the use thereof in large volume determinations utilizing automated equipment is feasible. The use of such equipment permits the screening on a large scale, e.g. in schools, institutions, etc. for individuals with indication of occult hyperlipidemia. Such individuals can then be tested in a more definitive manner, e.g. to determine the cholesterol and triglyceride levels in their serum.

In addition to being amenable to automated testing procedures and to the determination of a linear calibration curve, the method of beta-lipoprotein determination in accordance with the present invention exhibits excellent precision and reproducibility of results and exceptional specificity. The specificity of sodium polyanethole sulfonate as a beta-lipoprotein precipitating agent is an indication that the beta-lipoprotein determination will not be affected by the presence of excess concentrations of chylomicrons in the sera to be tested. In an experiment to determine the possible effect of chylomicrons on the lipoprotein test system of the subject invention it was demonstrated that, utilizing serum containing six times the normal amount of chylomicrons, the chylomicrons contributed only 0.5% of the total turbidity measured. This amount is readily corrected for, using the serum blank described earlier. In a comparative test under the same conditions, it was found that between 3.4 and 5.0% of the total turbidity measured utilizing a commercial preparation for determination of beta-lipoprotein was attributable to the chylomicrons. The procedure for this preparation does not include the preparation of a serum blank. It is therefore readily apparent that the standard or reference for serum beta-lipoprotein determination as well as the method and reagent kit embodying same are, unexpectedly, significantly advantageous in comparison with state of the art preparations.

The following examples further illustrate the invention.

EXAMPLE 1

A calibration standard reagent for the determination of serum beta-lipoprotein was prepared as follows: A total of 5.0 grams sodium polyanethole sulfonate was dissolved in 1 liter of serum with stirring at room temperature. To this solution was added 21.0 grams magnesium chloride hexahydrate (103 mmol/liter) and the mixture stirred until solution was effected. The resulting cloudy solution was allowed to stand at room temperature for one hour and was then centrifuged at 6000 xg for 20 minutes.

The precipitated lipoprotein thus obtained was suspended in 300 ml of water and 21 g. tetrasodium ethylenediaminetetraacetate (55 mmol/liter) added thereto with stirring. The mixture was diluted to one liter, warmed to 37° C and held at that temperature for one hour and centrifuged for 20 minutes at 5000 xg. The decanted clear yellow supernate was treated with an additional 21.0 g. of magnesium chloride hexahydrate to reprecipitate the lipoprotein. The mixture was centrifuged and the precipitate redissolved in a solution of 21 g. $Na_4$EDTA in 300 ml of distilled water. The resulting turbid solution was dialyzed for 48 hours against running tap water and concentrated to about 300 ml. About 500 mg of the lipoprotein mixture was placed on top of a DEAE-cellulose column which had been equilibrated with Tris-HCl (50 mmol/liter), pH 8.0, containing 100 mmol/liter sodium chloride. The column was eluded with Tris-HCl (50 mmol/liter), pH 7.0, containing 300 mmol/liter sodium chloride collecting 10 ml fractions of turbid lipoprotein solution. The fractions were combined, concentrated, centrifuged at 46,000 xg and the clear yellow supernate aspirated. The protein content of the calibration standard was again determined and adjusted to 1,000 ± 250 mg/dl.

EXAMPLE 2

Reagents were prepared for a serum beta-lipoprotein determination as follows:

Precipitant Reagent: 5.0 g. of sodium polyanethole, 21.0 g. magnesium chloride hexahydrate and 0.2 g. sodium azide were dissolved in 800 ml. of de-ionized water and the resulting solution diluted to one liter.

Reagent Blank: 21.0 g. magnesium chloride hexahydrate and 0.2 g. sodium azide were dissolved in 800 ml of de-ionized water and diluted to one liter.

A beta-lipoprotein calibration curve was prepared by adding 25-, 50-, and 100- microliter aliquots of the calibration standard prepared in Example 1 to 5.0 ml aliquots of the precipitant reagent solution with vortex mixing. The solutions were allowed to stand 15 minutes at room temperature and the turbidity was measured at 600 nm against the precipitant reagent solution. The turbidities in arbitrary absorbance units were plotted vs. mg. beta-lipoprotein/dl. Turbidity was measured in 12x75 mm cuvettes in a Coleman II Spectrophotometer equipped with a digital absorption-concentration meter and printer.

EXAMPLE 3

The reagents prepared in Example 2 were utilized in the determination of serum beta-lipoprotein content as follows. To 5.0 of the precipitant reagent was added 100 microliters fresh serum with vortex stirring. The mixture was allowed to stand at room temperature for 15 minutes and the turbidity measured vs. the precipitant reagent at 600 nm. Wherein the sera to be tested was cloudy and turbid, a serum blank was prepared by mixing 100 microliters of serum with 5.0 ml reagent blank solution and measuring the turbidity thereof at 600 nm. This solution is then utilized to correct the turbidimetric readings on the serum readings, if necessary.

A laboratory automated manifold and flow apparatus similar to but simpler than that described by Lopez et al., *Clin. Chem.* Vol. 17, p. 994 (1971) was utilized to determine samples at the rate of 60 specimens/hr (1:2 sample-to-wash ratio). Initially, aliquots of several levels of the calibration standard were analyzed in the apparatus to establish a calibration curve. Thereafter, sera specimens were analyzed. It was observed that following the manual procedure exactly did not produce optimum linearity of readings. This problem was solved by prediluting the serum sample in situ with water as opposed to saline and utilizing a more concentrated solution of sodium polyanethole sulfonate, i.e. a double ratio of sodium polyanethole sulfonate to serum.

The calibration curves in both the manual and automated determinations were linear with increasing protein content. Sera obtained from 25 subjects of both sexes age 20 to 60 and in apparent good health were assayed manually for beta-lipoprotein. Thirteen of these sera, randomly selected, were analyzed by the automated technique. The mean for the manual technique was 433 ± 96 (1 s.d.) mg beta-lipoprotein/dl and for the automated technique 412 ± 109 (1 s.d.) mg beta-lipoprotein. The results of a paired $t$ test showed no significant difference between the manual and automated techniques ($t_{12}=0.9$, critical value 2.18).

EXAMPLE 4

In order to demonstrate precision of the determination utilizing the beta-lipoprotein calibration standard described herein, several beta-lipoprotein standard solutions containing 200 mg/dl, 400 mg/dl and 800 mg/dl beta-lipoprotein, respectively, were assayed 12 times. A mean coefficient of variation of 2.2% was calculated.

Reproducibility of results with a series of sera was demonstrated using sera obtained from 6 healthy subjects and one patient analyzed daily over a 7-day period. A mean coefficient of variation of 10.3% was calculated. These sera were subdivided and placed under refrigeration and reanalyzed at weekly intervals for a month. The experiment established that the calibration standard and the sera are stable for at least a month under refrigeration. The results of this experiment are given in the following table.

Table

| Sample No | Lipoprotein mg/dl | Standard Deviation | Coefficient of Variation (%) | Day 7 mg/dl | Day 14 mg/dl | Day 21 mg/dl | Day 28 mg/dl |
|---|---|---|---|---|---|---|---|
| 1 | 564 | 29 | 5.1 | 537 | 561 | 531 | 584 |
| 2 | 468 | 50 | 10.7 | 453 | 461 | 445 | 427 |
| 3 | 400 | 26 | 6.5 | 397 | 394 | 399 | 424 |
| 4 | 406 | 47 | 11.6 | 412 | 444 | 439 | 455 |
| 5 | 392 | 76 | 19.4 | 380 | 345 | 350 | 354 |
| 6 | 443 | 44 | 9.9 | 467 | 458 | 459 | 502 |
| 7 | 697 | 61 | 8.8 | 715 | 721 | 692 | 734 |

EXAMPLE 5

In order to demonstrate the specificity of the assay described herein and the effect thereon of normal and increased chylomicron concentration in the serum, the following experiment was carried out.

A total of 7.0 ml of chylomicrons was isolated from 40 ml of pooled sera from several normal subjects of both sexes by subjecting the sera to centrifugation for 45 minutes at 100,000 xg. Using electrophoretic techniques, the whole sera of these individuals prior to isolation of the chylomicrons appeared normal. Turbidimetric assay showed the lipoprotein content of the sera of these individuals to be within normal limits, i.e. 300–500 mg/dl. Aliquots of the chylomicron preparation were carried through the lipoprotein test as were reagent blanks. The results are given in the following table:

Table

| Chylomicrons Aliquot (ml) | Whole Serum Equivalent (ml) | Absorption (test) | Absorption (blank) | Difference | Apparent LP content (mg/dl) | Whole Serum Test Equivalent (mg/dl) | % of Normal* |
|---|---|---|---|---|---|---|---|
| 0.1 | 0.7 | 0.019 | 0.013 | 0.006 | 18 | 2.6 | 0.6 |
| 0.2 | 1.4 | 0.047 | 0.038 | 0.009 | 28 | 2.0 | 0.5 |
| 0.5 | 3.5 | 0.122 | 0.067 | 0.059 | 181 | 5.2 | 1.3 |

The results in the table indicate that, using the 0.1 ml serum specimen, serum containing six times the normal amount of chylomicrons contributes only 0.5% of the total turbidity measured. This amount is readily corrected for utilizing the serum blank.

We claim:

1. In a process of isolating beta-lipoproteins from blood serum by contacting serum with a polyanion in the presence of a divalent cation, the improvement which comprises obtaining said beta-lipoproteins in about 99% purity and substantially free of chylomicrons by:

(a) contacting blood serum with a sufficient amount of a solution containing about 0.5% by weight polyanethole sulfonate and from about 0.05 to about 0.15 mole per liter of a divalent cation to precipitate the beta-lipoproteins therein substantially free of chylomicrons;

(b) forming a solution of said beta-lipoproteins and reprecipitating them with said divalent cation to further purify them; and (c) passing a solution of said beta-lipoproteins through a DEAE-cellulose column to effect immunochemical purification thereof.

2. The improved method of claim 1 wherein said divalent cation is $Mg^{++}$.

3. In a method of determining the beta-lipoprotein content of serum which comprises contacting a serum specimen with polyanion and a divalent cation, determining the turbidity of the specimen and comparing said turbidity against the turbidity of a calibration standard containing a known amount of beta-lipoprotein, the improvement which comprises contacting the serum sample with sodium polyethanole sulfonate and a divalent cation and utilizing as the calibration standard, the purified beta-lipoprotein composition prepared by the process of claim 1.

* * * * *